(12) United States Patent
Papadimitriou

(10) Patent No.: US 8,519,098 B2
(45) Date of Patent: Aug. 27, 2013

(54) COMPOSITION OF A POLYPEPTIDE AND AN AMPHIPHILIC COMPOUND IN AN IONIC COMPLEX AND THE USE THEREOF

(75) Inventor: Apollon Papadimitriou, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 1126 days.

(21) Appl. No.: 11/931,118

(22) Filed: Oct. 31, 2007

(65) Prior Publication Data

US 2008/0064854 A1    Mar. 13, 2008

Related U.S. Application Data

(60) Continuation of application No. 11/032,492, filed on Jan. 10, 2005, now abandoned, which is a continuation of application No. 09/953,721, filed on Sep. 17, 2001, now Pat. No. 6,867,182, which is a division of application No. 09/385,404, filed on Aug. 30, 1999, now abandoned.

(30) Foreign Application Priority Data

Sep. 1, 1998    (EP) .................................... 98116494

(51) Int. Cl.
*A61K 9/14*    (2006.01)
*A61K 9/19*    (2006.01)
*A61K 9/24*    (2006.01)
*A61K 47/12*    (2006.01)

(52) U.S. Cl.
USPC .......................... 530/350; 514/1.1; 514/21.92

(58) Field of Classification Search
None
See application file for complete search history.

(56) References Cited

U.S. PATENT DOCUMENTS

| | | | |
|---|---|---|---|
| 4,604,377 A | 8/1986 | Fernandes et al. | |
| 5,109,038 A | 4/1992 | Chauvel et al. | |
| 5,124,081 A | 6/1992 | Vanlerberghe et al. | |
| 5,650,393 A | 7/1997 | Pavia et al. | |
| 5,653,987 A * | 8/1997 | Modi et al. | 424/400 |
| 5,665,328 A | 9/1997 | Horan et al. | |
| 5,688,761 A | 11/1997 | Owen et al. | |
| 5,853,748 A | 12/1998 | New | |
| 5,952,008 A | 9/1999 | Backstrom et al. | |
| 6,630,148 B1 * | 10/2003 | Ingham et al. | 424/185.1 |

FOREIGN PATENT DOCUMENTS

| | | |
|---|---|---|
| AU | 199915426 | 8/1999 |
| CA | 2309806 | 6/1998 |
| CA | 2269221 | 10/1999 |
| EP | 179 583 | 4/1986 |
| EP | 874 048 | 10/1998 |
| EP | 917 879 | 5/1999 |
| EP | 919 618 | 6/1999 |
| EP | 947 201 | 10/1999 |
| EP | 953 576 | 11/1999 |
| JP | 61500790 | 4/1986 |
| JP | 6289627 | 4/1987 |
| JP | 62207226 | 9/1987 |
| JP | 2096553 | 4/1990 |
| WO | WO 85 04328 | 10/1985 |
| WO | WO 94 08599 | 4/1994 |
| WO | WO 95/18601 | 7/1995 |
| WO | WO 95 18856 | 7/1995 |
| WO | WO 96 36352 | 11/1996 |
| WO | WO 98/16555 | 4/1998 |
| WO | WO 98 21227 | 5/1998 |
| WO | WO 98 30234 | 7/1998 |
| WO | WO 98 30576 | 7/1998 |
| WO | WO 99 20298 | 4/1999 |

OTHER PUBLICATIONS

Pepinsky, R. Blake; et al., The Journal of Biological Chemistry, v. 273, pp. 14037-14045 (1998).
Hammerschmidt, Matthias, Trends in Genetics, 13, pp. 14-21 (1997).
Tomlinson et al., J. of Colloid and Interface Science, vol. 74, No. 2, (1980), p. 349-359.
Cools et al., J. Pharm. Pharmacol., 35 (1983) p. 689-691.
Hirai et al., Int. J. Pharm., 7 (1981), p. 317-325.
Okada et al., J. of Pharm. Science, vol. 72, No. 1 (1983), p. 75-78.
Mazzenga et al., J. of Controlled Release, 16 (1991), p. 77-88.
Lee et al., Critical Rev. Therp. Drug Carrier Systems 8 (1991), p. 91-192.
Morimoto et al., Arch. Int. Pharmacodyn., 302 (1989), p. 18-26.
Aungst et al., Int. J. of Pharm., 33 (1986), p. 225-234.
Womack et al., Biochim. of Biophys. Acta, 733 (1983), p. 210-215.
Ekrami et al., FEBS Letters, 371 (1995), p. 283-286.
Marti et al., Nature, vol. 375, p. 322-325 (1995).
Yang et al., Development, vol. 124, p. 4393-4404 (1997).
Lopez-Martinez et al., Current Biology, vol. 5, p. 791-796 (1995).
Kinto et al., FEBS Letter, vol. 404, p. 319-323 (1997).
Database Caplus, DN 106:162592; Matsuda et al., JP 61293926 (1986).
Manning et al., Biotechnology and Bioengineering, 48, pp. 506-512 (1995).
An English Translation of a Japanese Office Action relating to Japanese Patent Application No. HEI 11-248013 corresponding to the instant U.S. Patent Application, 2003.
An English Translation of a Taiwanese Office Action relating to Taiwanese Patent Application No. 088114073 corresponding to the instant U.S. Patent Application, 2003.
A Canadian Office Action relating to Canadian Patent Application No. 2,281,049 corresponding to the instant U.S. Patent Application, 2002.
An English Translation of an Ecuadorian Office Action relating to Patent Application No. SP 99 3199 corresponding to the instant U.S. Patent Application, 2004.
A European Office Action in English text relating to Patent Application No. 99119245.1 corresponding to the instant U.S. Patent Application, 2005.

\* cited by examiner

*Primary Examiner* — Michael Borin

(57) ABSTRACT

An ionic complex precipitate comprising a hedgehog protein and deoxycholate whereby the forming of the complex does not enhance the solubility of said protein, is suitable for increasing the activity of the protein and/or for the delayed release of the protein.

9 Claims, 1 Drawing Sheet

COMPOSITION OF A POLYPEPTIDE AND AN AMPHIPHILIC COMPOUND IN AN IONIC COMPLEX AND THE USE THEREOF

PRIORITY TO RELATED APPLICATIONS

This application is a continuation of U.S. application Ser. No. 11/032,492, filed Jan. 10, 2005, pending, which is a continuation of U.S. application Ser. No. 09/953,721, filed Sep. 17, 2001, now U.S. Pat. No. 6,867,182, which is a division of U.S. application Ser. No. 09/385,404, filed Aug. 30, 1999, now abandoned, which claims the benefit of European Application No. 98116494.0, filed Sep. 1, 1998; all of which are hereby incorporated herein by reference in their entirety.

BACKGROUND OF THE INVENTION

The use of amphiphilic compounds as a drug delivery system is well known in the state of the art (cf. U.S. Pat. No. 5,650,393; U.S. Pat. No. 5,688,761; U.S. Pat. No. 5,665,328; U.S. Pat. No. 5,124,081; U.S. Pat. No. 5,109,038). Formation of complexes in the form of micelles between surface-active substances and pharmaceutical agents is also known for example for improving the transdermal and transmembrane penetration of the active agent (Tomlinson and Davis, J. Colloid. Interf., Sci. 74 (1980) 349). It is also known that pharmaceutical agents usually have better transport properties through biological membranes in their non-ionized form than in the ionized state (Cools and Jansen, J. Pharm. Pharmacol. 35 (1983) 689-691). It is also known that peptides which are present in a multiple ionized form at physiological pH values, are also not optimal for transport to the site of action (drug delivery) since charged molecules and in particular polypeptides have a low solubility in lipids (Hirai et al., Int. J. Pharm. 7 (1991) 317-325). It is known from Okada et al., J. Pharm. Sci. 72 (1993) 75-78 that it is advantageous to bind a lipophilic counterion to the ionic part of the agent and thus improve the interaction with the biological membrane in order to facilitate transport of proteins through intestinal membranes. For example Hazzenga and Berner describe an improved method for the transdermal transport of zwitterionic active agents in J. Controlled Release 16 (1991) 77-88.

Other methods for improving the interaction of agents with biological membranes are described for example by Lee et al., Critical Rev. Therp. Drug Carrier Systems 8 (1991) 91-192, Morimoto et al., Arch. Int. Pharmacodyn. 302 (1989) 18-26 and Aungst, Int. J. Pharm. 33 (1986) 225-234. However, in all these methods the aim was to increase the hydrophobicity of the active agent in order to facilitate its penetration through biological membranes such as skin and deliver said agent into the cell. The surface-active substances are used for this at a concentration which was above the critical micelle concentration (CMC, Womack et al., Biochim. Biophys. Acta 733 (1983) 210). A disadvantage of such methods is that the high concentrations of the surface-active substances that are used have a massive influence on the cell membrane and may damage it.

It is known from WO 94/08599 that a homogeneous solution of an active agent can be prepared for the production of carrier-bound active agents by adding an adequate amount of an anionic detergent to form a precipitate, isolating the precipitate and dissolving it again in an organic solvent. This homogeneous solution which contains a complex between the anionic detergent and the active agent can then be used to embed or disperse the active agent in a solid matrix. In addition WO 94/08599 mentions that a complex of the protein with an anionic detergent can be formed and the active agent can be released from it for the controlled release of a protein.

It is known that the activity of proteins can be improved by covalent coupling to hydrophobic compounds such as fatty acids or steroids. However, such methods are complicated and lead to inhomogeneous products due to the chemical reaction of the coupling (cf. e.g. Ekrami, H. M. et al., FEBS Letters 371 (1995) 283-286, Pepinski, R. B. et al., J. Biol. Chem. 273 (1998) 14037-14045).

SUMMARY OF THE INVENTION

This invention provides a composition comprising an aqueous buffered solution having a protein and an amphiphilic agent dissolved therein, wherein the protein is selected from the group consisting of hedgehog proteins, bone morphogenetic proteins, growth factors, erythropoietin, thrombopoietin, G-CSF, interleukins, and interferons; the protein is at a concentration of from 0.1 to 10 mg/ml in the solution; the amphiphilic compound is at a concentration of at least 0.001 to 0.1% weight per volume in the solution; the solution is buffered with a buffer to a pH of from 4 to 10 when measured at a temperature of from 4° C. to 30° C.; and the buffer is present in the solution in a concentration of from 10 to 500 mmol/liter in the solution.

The compositions in accordance with this invention improve the activity of the cell surface active protein contained therein. It is believed that the increase in biological activity results from the formation of an ionic complex between the protein and the amphiphilic compound. Accordingly, the invention further provides a method of increasing the activity of cell surface active proteins. In addition, the invention provides solid storage forms of such proteins and uses of the composition of this invention. The compositions of this invention can be used in the same way as the proteins contained therein are used, for example in in vitro assays, diagnostic methods and as therapeutic substances.

DETAILED DESCRIPTION OF THE INVENTION

Figure 1:
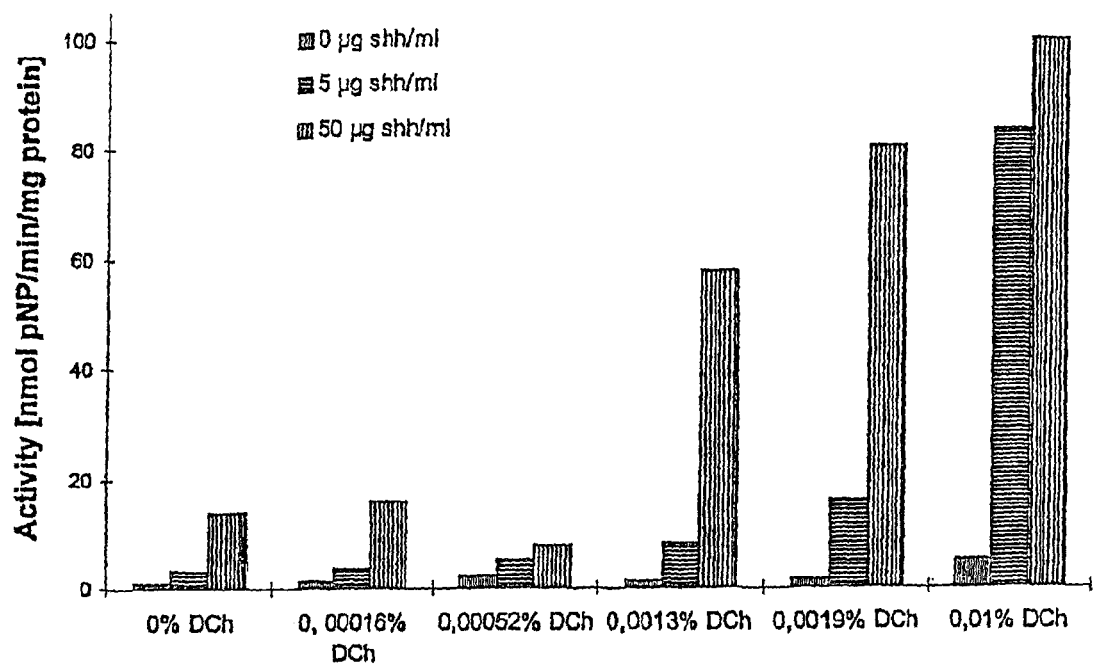
FIG. 1 shows the dependency of the induction of alkaline phosphatase in a cell test by shh on increasing concentrations of deoxycholate.

This invention provides a composition, preferably a pharmaceutical composition, containing a pharmaceutically effective polypeptide selected from the group consisting of hedgehog proteins, bone morphogenetic proteins, growth factors, erythropoietin, thrombopoietin, G-CSF, interleukins and interferons, characterized in that said composition contains, in addition, an amphiphilic compound, said polypeptide and said amphiphilic compound forming an ionic complex, whereby the forming of the complex does not enhance the solubility of said polypeptide. The composition does not contain any organic solvent. For storage purposes the composition can be lyophilized.

In the invention, the polypeptide and the amphiphilic compound are individually soluble at the concentrations used in aqueous, preferably buffered solutions, and it is only the combination of the two substances that results in the formation of a complex by means of ionic interactions which hydrophobizes the polypeptide and thus worsens or at least does not improve its water-solubility. It has surprisingly turned out that in this manner the activity of such polypeptides can be significantly improved.

According to the invention the amount and ratio of the amphiphilic compound and the polypeptide are selected preferably in such a way that the aqueous composition containing the ionic complex is a clear solution. If the complex formation between the polypeptide and the amphiphilic compound results in turbidity, then the solution is filtered to give a turbidity-free solution, if the composition will be used directly as a solution for administration to a patient. If the composition will be immobilized on a carrier prior to administration to the patient, turbidity need not be avoided.

The pharmaceutically effective polypeptide is a polypeptide which can be present in an ionic form and which is recognized and bound by a cell surface receptor (extracellular receptor) to develop its biological activity. Such polypeptides are growth factors (e.g. NGF, TGF-β, FGF, GDF, insulin-like growth factors), erythropoietin, thrombopoietin, G-CSF, interferons such as Interferon-α2b, interleukins such as Interleukin-2 or Interleukin-12, bone morphogenetic proteins such as BMP-2, or hedgehog proteins such as sonic, indian or desert hedgehog proteins. Especially preferred are hedgehog proteins. Polypeptides are preferably used which have an activity (therapeutic effect and/or protein activity in vitro) that is increased preferably 10-fold or more in the complex according to the invention compared to the uncomplexed form. The ionic form of the polypeptide can be obtained by its being present in an environment which advantageously differs by at least an 0.5 pH unit from its pK value.

The amphiphilic compound according to the invention is to be understood as an anionic, zwitterionic or cationic hydrophobic surfactant, a fatty acid, an alkyl sulfonate or a lipid. In accordance with this invention any amphiphilic compound can be utilized. Preferred anionic surfactants are anionic detergents such as steroidic tensides like deoxycholates, cholates, taurocholates, taurodeoxcholates, dehydrocholates (useful for cationic polypeptides); preferred zwitterionic surfactants are CHAPS (3[(3-cholamidopropyl)dimethylammonio]-1-propane sulfonate) and Zwittergent® (N-dodecyl-N, N-dimethyl-3-ammonio-1-propane sulfonate); and preferred cationic detergents are cetyltrimethylammonium bromide or dodecylammonium chloride (useful for anionic polypeptides); preferred fatty acids are fatty acids such as palmitic acid (useful for cationic polypeptides). Preferred alkyl sulfates are alkyl sulfonates such as decyl sulfonate (useful for cationic polypeptides); and preferred lipids are lipids such as phosphatidyl serine and phosphatidate (useful for cationic polypeptides).

The amphiphilic compound is added to the composition under conditions which hydrophobise the polypeptide and therefore reduce, or at least do not improve, the water-solubility of the polypeptide. It is important that according to the invention a water-soluble ionic complex between the polypeptide and amphiphilic compound is formed in this process. The ratio of polypeptide to amphiphilic compound in the complex depends on the pH value used and the pK values of the two substances and on the concentration ratio. A pH value is preferably used which differs by at least one half pH unit from the pK values of the polypeptide and of the auxiliary substance. The more amphiphilic compound is added, the more amphiphilic compound binds to the polypeptide and the more hydrophobic the complex becomes. This can lead to precipitation of the complex and hence the presence of a mixture of soluble and insoluble complex which is no longer completely water-soluble. The addition of a non-ionic detergent such as of a polyoxamer like Tween® can, however, at least partly restore the water-solubility of the complex, or the composition can be filtered, if necessary. In this case the non-ionic detergent can also be present at concentrations which lead to micelle formation. It must be noted that the type and concentration of the amphiphilic compound are selected such that, especially with proteins as a polypeptide, the molecular structure of the polypeptide is retained in its natural active form and thus the activity of the polypeptide is not reduced. Usually a 10-fold molar excess of amphiphilic compound is sufficient for this purpose. Preferably, with a protein amount of 5 μg protein per ml, 0.001 to 0.05% (weight per volume) of amphiphilic compound are added. When the protein is a hedgehog protein in a concentration of about 1 mg/ml in phosphate buffer solution, pH 7.4, and the amphiphilic agent is cholate, deoxycholate, taurocholate or taurodeoxycholate, the optimal concentration of the amphiphilic agent is from 0.001 to 0.1% (w/v) in the solution. When the amphiphilic agent is phosphatidate, phosphatidylserine or sodium palmitate, the optimal concentration of the amphiphilic agent is from 0.001 to 0.05% (w/v) in the solution.

If a denaturing surfactant such as sodium dodecyl sulfate (SDS) is for example used according to the invention, this compound can only be used at low concentrations. It is known that SDS denatures proteins at high concentrations which improves the water-solubility of these proteins but in a denatured inactive form. Such amphiphilic compounds like SDS can also form micelles at higher concentrations in addition to the desired complexes according to the invention which then in turn increase the solubility of the polypeptide. Whether the amphiphilic compound causes an undesired denaturation of the polypeptide can be easily determined by methods familiar to a person skilled in the art. Such methods are for example activity determination or physicochemical methods for checking the structure such as IR, CD and fluorescence spectroscopy.

An aqueous water-soluble pharmaceutical composition in the sense of the invention is to be understood as a composition which essentially comprises no insoluble particles which contain the pharmaceutically effective polypeptide. In particular an aqueous pharmaceutical composition is to be understood according to the invention as a composition which does not have visible turbidity. Such soluble compositions are possible when the ionic complex according to the invention is completely water-soluble at the concentrations used of polypeptide and surfactant or undissolved complex is removed by filtration. According to the invention, the aqueous composition does not contain in addition organic solvents. Moreover, it might be necessary, for the manufacture of the compositions, to solve such amphiphilic compounds like fatty acids in a small amount of organic solvent (up to 5%, preferably up to 1% of the volume of the composition).

An additional subject matter of the invention is a process for producing an aqueous pharmaceutical composition according to the invention which is characterized in that a pharmaceutically effective polypeptide and an amphiphilic compound which worsens or at least does not improve the water-solubility of the pharmaceutically effective polypeptide are combined in such a concentration ratio and at such a pH value that an ionic complex forms between the polypeptide and auxiliary substance by ionic interaction.

A further subject matter of the invention is the use of the pharmaceutical composition according to the invention for a systemic or local administration to the body of humans or mammals.

In a preferred embodiment a hedgehog protein is used in the pharmaceutical composition as the pharmaceutically effective polypeptide. It is known that the activity of hedgehog proteins can be improved by covalent hydrophobic modification (European Patent Application No. 99108032.6).

According to the invention it has surprisingly turned out that the activity of hedgehog proteins can be increased to a considerable extent by forming an ionic complex between a hedgehog protein and an amphiphilic compound. In a preferred embodiment an increase in the activity of the hedgehog protein (compared to a recombinant hedgehog protein produced in E. coli) by 10-fold or more is obtained.

Consequently a preferred subject matter of the invention is a pharmaceutical composition containing a complex of a hedgehog protein and an amphiphilic compound formed by ionic interactions wherein the compound is present at a concentration which worsens or at least does not improve the solubility of the said hedgehog protein.

Hedgehog (hh) proteins are understood as a family of secreted signal proteins which are responsible for the formation of numerous structures in embryogenesis (J. C. Smith, Cell 76 (1994) 193-196, N. Perrimon, Cell 80 (1995) 517-520, C. Chiang et al., Nature 83 (1996) 407, M. J. Bitgood et al., Curr. Biol. 6 (1996) 296, A. Vortkamp et al., Science 273 (1996) 613, C. J. Lai et al., Development 121 (1995) 2349). During its biosynthesis a 20 kD N-terminal domain and a 25 kD C-terminal domain are obtained after cleavage of the signal sequence and autocatalytic cleavage. In its natural form the N-terminal domain is modified with cholesterol and palmitoyl (J. A. Porter et al., Science 274 (1996) 255-259 and Pepinski et al., J. Biol. Chem. 273 (1998) 14037-14045). In higher life-forms the hh family is composed of at least three members namely sonic, indian and desert hh (Shh, Ihh, Dhh; M. Fietz et al., Development (Suppl.) (1994) 43-51). Differences in the activity of hedgehog proteins that were produced recombinantly were observed after production in prokaryotes and eukaryotes (M. Hynes et al., Neuron 15 (1995) 35-44 and T. Nakamura et al., Biochem. Biophys. Res. Comm. 237 (1997) 465-469).

Sonic, indian or desert hh are particularly preferably used (Fietz M. et al., Development (Suppl.) (1994) 43-51). A hh protein having a sequence described in the EMBL data bank under the No. L38518 is preferably used. Proteins of the hedgehog family have a pronounced homology in their amino acid sequence which is why it is also preferable to express those nucleic acids which code for hedgehog proteins that are 80% or more homologous to the above-mentioned sequence of sonic hedgehog protein. Hedgehog proteins are preferably used as they are for example described in the International Application No. WO 99/28454 and in European Patent Application No. 99108032.6.

The human sonic hedgehog precursor protein is composed of the amino acids 1-462 of the sequence described in the EMBL databank under No. L38518. The amino acids 1-23 represent the signal peptide, the amino acids 24-197 represent the mature signal domain, the amino acids 32-197 represent the signal domain shortened by eight amino acids and the amino acids 198-462 represent the autoprocessed C-terminal domain after autoproteolytic cleavage.

Pharmaceutical effect of the hedgehog protein is preferably understood as a neurological effect on nerve cells, preferably osteogenesis and/or osteoinduction, and especially preferably chondrogenesis and/or chondroinduction as described in Kinto et al., FEBS Letters, 404 (1997) 319-323 for bone induction, by Miao et al. in J. Neurosci. 17 (1997) 5891-5899 for the effect on nerve cells and by Stott et al. in J. Cell Sci. 110 (1997) 2691-2701 for cartilage cell induction.

Solutions of the hedgehog proteins at high concentrations are necessary to prepare carrier matrices that are coated or embedded with the complexes according to the invention in such a manner that they have an adequate pharmaceutical efficacy for a local application. It has turned out that carriers that can be used pharmaceutically should preferably contain a concentration of the hedgehog protein of 0.1-10 mg/ml carrier and more. Hedgehog proteins are intrinsically poorly soluble. It has, however, surprisingly turned out that the solubility of hedgehog proteins is drastically increased and the stability of hh proteins is improved at low concentrations (<1 mg/ml or less) in solutions which contain arginine or argininium ions. It is therefore preferable to add arginine or argininium ions to the aqueous solution and to the carrier bound complex.

Activity of the hedgehog protein within the sense of the invention is understood as the activity of alkaline phosphatase (stimulation of the expression of alkaline phosphatase) which the polypeptide can induce in mammalian cells (activity in the alkaline phosphatase test). In this method a mouse fibroblast cell line is cultured in a medium which contains foetal calf serum. Subsequently sterile filtered sample is added, the cells are lysed after ca. 5 days and alkaline phosphatase is determined in the cell lysate by means of the cleavage of a chromogenic substrate (pNP, p-nitrophenol) (J. Asahina, Exp. Cell. Res. 222 (1996) 38-47 and T. Nakamura (1997)).

The pharmaceutical composition according to the invention contains a pharmacologically effective dose of the hh protein and can be administered systemically or preferably locally. It is preferable to use the proteins according to the invention in combination with other proteins of the hedgehog family or bone growth factors such as bone morphogenetic proteins (BMPs) (Wozney et al., Cell. Mol. Biol. of Bone, Bone Morphogenetic Proteins and their Gene Expression (1993) Academic Press Inc., 131-167) or parathyroid hormones (Karablis et al., Genes and Development 8 (1994) 277-289) or insulin-like growth factors (IGF-I or II) or transforming growth factor family (TGF-β, GDF). These other proteins can also, but do not have to be, present in the complexes according to the invention.

Hence a further subject matter of the invention is a process for the production of a preferably water-soluble pharmaceutical composition of a hedgehog protein by combining the said hedgehog protein with an amphiphilic compound under conditions which allow an ionic complex to form between the hedgehog protein and the amphiphilic compound.

An additional subject matter of the invention is the use of such a complex of a hedgehog protein according to the invention to produce a pharmaceutical composition in which the complex is used as an essential component of the composition and is optionally combined with suitable additional pharmaceutical auxiliary substances, preferably in a buffered aqueous solution. In a further preferred embodiment the hedgehog complex according to the invention is present in a mixture of a dissolved and precipitated form or only in a precipitated form which enables a delayed release of the hedgehog protein or a local application at the site of action in vivo. Release of the protein at the site of action is slower from this mixture than from a completely dissolved pharmaceutical formulation.

Furthermore it is preferable for the production of the pharmaceutical composition to add auxiliary substances such as sodium chloride, sugars or sugar alcohols (mannitol, sucrose, lactose, trehalose, preferably 20-100 mg/ml) or amino acids such as glycine or arginine, methionine, cysteine as well as antioxidants such as EDTA, citrate, thioglycerol, acetylcysteine, polyethylene glycol (1-10% by weight), anti-inflammatory agents, local anaesthetics, antibiotics and/or stabilizers.

In a further preferred embodiment a pharmaceutical composition of the hedgehog protein according to the invention containing suramin is preferred and this can be used advantageously.

The pharmaceutical composition can contain additional pharmaceutical auxiliary substances and is preferably lyophilized.

In a preferred embodiment the pharmaceutical composition contains hedgehog protein at a concentration of 0.1-10 mg/ml, preferably 0.1-5 mg/ml. In a more specific embodiment, the concentration of the hedgehog protein is from 1-5 mg/ml.

In a preferred embodiment the pharmaceutical composition additionally contains a pharmaceutically acceptable buffer which is biocompatible, preferably in a range between pH 4 and pH 10, particularly preferably in a range between pH 6 and 8. The concentration of the buffer is preferably 10-500 mmol/l, more preferably 10-100 mmol/l. It is expedient to select the salt concentrations such that they do not interfere with the complex formation due to high ionic strength.

In another embodiment of the invention the pharmaceutical composition contains the complex according to the invention embedded in a carrier which is biocompatible and can for example be used as an implant. The carrier is preferably a polymer which does not denature the hedgehog protein when it is embedded in the carrier, has an average molecular weight of at least 10,000 Da.

Such polymers are, for example, hyaluronic acid, collagen, alginate or organic polymers such as PLGA (copolymer of polylactic and glycolic acid) or derivatives thereof. If the complex is embedded in a carrier it is not necessary that the complex is completely soluble in solution like it is useful for the aqueous pharmaceutical composition described above. As the carrier bound complex is applied locally in the body, preferably as a complex of hedgehog polypeptide in bone or cartilage, it is slowly released in soluble form from the complex, thus developing its desired biological effect.

A further subject matter of the invention is the use of the pharmaceutical composition according to the invention which is immobilized on (bound reversibly to) a biocompatible carrier for local application on the human body or on animals. Such biocompatible carriers are for example hyaluronic acid, collagen, alginate or organic polymers such as PLGA or derivatives thereof.

The complex according to the invention is preferably localized on a biocompatible carrier wherein the carrier can release the complex locally in vivo in an active form. Such formulations are especially suitable for the repair of bone and cartilage defects but can also be used to repair neuronal defects or for a systemic delivery.

The pharmaceutical composition according to the invention preferably contains a polymer which essentially acts as a structural substance which preferably also has an adhesion function for cells. Such a structural substance is for example collagen.

In a further preferred embodiment the pharmaceutical composition according to the invention is used to reduce systemic side-effects outside the desired site of action when administered locally. The local administration of a pharmaceutically effective polypeptide which is not completely immobilized or does not have an extremely short local half-life can lead to spreading of the polypeptide or at least a part of it beyond the desired site of action where it leads to undesired systemic actions. These undesired systemic effects can be considerably reduced or even avoided by the invention. The method is suitable for polypeptides which have a 10-fold or more increased activity in the ionic complex as compared to the uncomplexed form, wherein the complex has a lower solubility in a buffered aqueous solution than the uncomplexed polypeptide. Such polypeptides are preferably hedgehog proteins, cytokines and growth factors such as NGF.

According to the invention an ionic complex of the polypeptide and the amphiphilic compound is applied preferably locally in this method in such an amount that the polypeptide exhibits an activity in the complex which corresponds to its therapeutic dose (effective dose) in vivo. The amount of complex must be selected such that when the complex dissociates, which for example occurs when it is diluted 10- to 20-fold under physiological conditions e.g. in blood, the activity of the polypeptide is then only 20% or less of the therapeutic dose. Hence in such a local application of the complex according to the invention the pharmaceutically effective polypeptide exhibits its full therapeutic effect such as bone growth locally at the desired site of action when the polypeptide is a bone growth factor such as a cytostatic or apoptosis-inducing effect when the polypeptide is a tumoricidal agent. When the complex diffuses from the site of action, the complex is diluted under the physiological conditions prevailing outside the site of action which leads to dissociation. This results in a decrease of the concentration of the complexed polypeptide and an increase in the concentration of non-complexed polypeptide. Since the activity of the non-complexed polypeptide is considerably less than that of the complexed polypeptide, its therapeutic effect is also reduced outside the site of action.

A further subject matter of the invention is the use of a pharmaceutical composition according to the invention for local application in humans characterized in that the complex is administered in such an amount that the complexed polypeptide exhibits an activity which corresponds to its therapeutic dose whereby the same amount of polypeptide in an uncomplexed form would exhibit an activity of 20% or less of the therapeutic dose.

A further subject matter of the invention is a process for the production of a pharmaceutical composition for local administration in humans characterized in that a complex of a pharmaceutically effective polypeptide and of an amphiphilic compound formed by ionic interaction is used as an essential component, in which the compound is present at a concentration which worsens the water-solubility of the pharmaceutically effective polypeptide and the complex is administered in an amount in which the complexed polypeptide exhibits an activity which corresponds to its therapeutic dose whereas the same amount of polypeptide in an uncomplexed form would exhibit an activity of 20% or less of the therapeutic dose.

In accordance with the composition described herein this invention provides a method for increasing the activity of a cell surface active protein, comprising: a) dissolving the protein in an aqueous solution; and b) adjusting the aqueous solution with an amphiphilic compound and a buffer so that the aqueous solution having the protein dissolved therein contains the protein at a concentration of from 0.1 to 10 mg/ml; contains the amphiphilic compound at a concentration of at least 0.001 to 0.1% weight per volume; is buffered with the buffer to a pH of from 4 to 10 when measured at a temperature of from 4° C. to 30° C.; and contains the buffer in a concentration of from 10 to 500 mmol/liter. Examples of such cell surface active proteins include hedgehog proteins, bone morphogenetic proteins, growth factors, erythropoietin, thrombopoietin, G-CSF, interleukins, and interferons.

The contents of European Patent Application No. 98116494.0, filed Sep. 1, 1998, are incorporated herein by reference.

The following examples, publications and the figures further elucidate the invention, the protective scope of which results from the patent claims. The described methods are to be understood as examples which still describe the subject matter of the invention even after modifications.

Example 1

Analysis of the Activity of Different Hedgehog Formulations in a Cell Test: Induction of Alkaline Phosphatase 5000 cells of the murine mesenchymal plutipotent line C3H10T1/2 (ATCC CCL-226) are sown in each well of a 96-well microtitre plate. The cells are in DMEM, 2 mM glutamine, 100 IU penicillin/ml, 100 μg streptomycin/ml and 10% foetal calf serum. On the next day the medium is replaced by medium which contains human shh (0, 5 or 50 μg/ml) in different formulations (0, 0.00016, 0.00052, 0.0013, 0.0019 or 0.01% sodium deoxycholate), or the various hedgehog formulations are added directly. The test is stopped after 5 days. For this the supernatants are decanted and the cells are washed once with PBS. The cells are lysed in 50 μl 0.1% Triton® X-100 and frozen at −20° C. After thawing, 25 μl aliquots are used for protein determination and to determine the activity of alkaline phosphatase.

Protein Determination According to the Instructions of the Manufacturer Pierce:

75 μl redistilled $H_2O$ is added to the mixture, then 100 μl BCA protein reagent is added (Pierce Micro BCA, No. 23225). The absorbance is measured at 550 nm after 60 min.

Determination of the Alkaline Phosphatase Activity According to the Instructions of the Manufacturer Sigma:

100 μl reaction buffer (Sigma 221) is added to the mixture. A substrate capsule (Sigma 104-40) is dissolved in 10 ml $H_2O$, then 100 μl is added by pipette to the test mixture. The absorbance is measured at 405 nm. During the reaction alkaline phosphatase converts p-nitrophenylphosphate to p-nitrophenol (pNP). The measured absorbances are converted into nmol pNP by means of standard curves.

The activities of various hedgehog formulations in nmol pNP/min/mg protein are plotted in FIG. 1. This shows that, at the same protein concentrations, the activities of the examined hedgehog formulations increased considerably with increasing deoxycholate concentrations.

Example 2

Hydrophobic Ion Pair Titration of hshh (Dimer)

Figure 2:
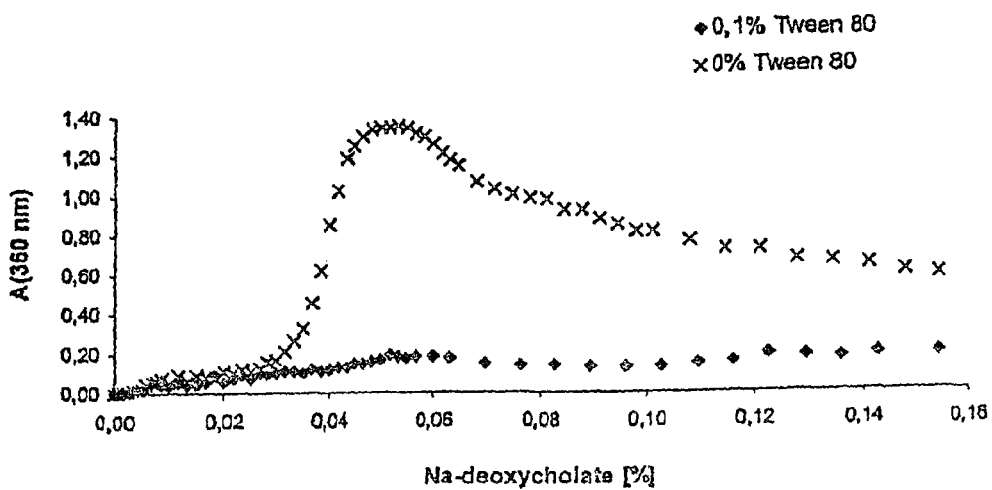
FIG. 2 shows the dependency of aggregate formation on the concentration of deoxycholate.

Recombinant human sonic hedgehog protein (dimer, 0.8 mg/ml in 50 mM Tris-Cl, pH 7.4 or in 0.1% Tween 80, 50 mM Tris-Cl, pH 7.4) is admixed with increasing concentrations of sodium deoxycholate. The absorbance at 360 nm is measured as an indicator for turbidity (formation of water-insoluble aggregates composed of ionic protein-detergent complexes). It is clear from FIG. 2 that the transition to water-insoluble aggregates occurs above ca. 0.04% Na deoxycholate. The formation of water-insoluble aggregates can be largely prevented in the presence of 0.1% Tween 80. The stated absorbances are not corrected for dilution.

Example 3

Analysis of NGF Formulations in a Bioactivity Assay: Dorsal Root Ganglion Neuron Development Assay NGF bioactivity was determined by morphometric analysis of dorsal root ganglion (DRG) neurons developing in vitro. Briefly, lumbar DRG's were dissected from E7-E8 embryonic chickens, freed from surrounding connective tissue and dissociated by triturgation through a fire polished pasteur pipette following digestion with 0.1% trypsin for 20 min at 37° C. Contaminating cells, such as fibroblasts were removed by preplating the entire cell preparation onto plastic tissue culture dishes for 2 h. Under these conditions neurons do not attach to the substrate, while fibroblasts and other non-neuronal cells adhere to the tissue culture plastic. "Clean" neurons were harvested by collecting the supernatant and plated onto poly-ornithine/laminin coated plastic dishes (48 wells) at a density of 10,000 cells/well in HAM's F14 medium containing 5% FBS. A dose-response curve for NGF was titrated from approximately 1 pg/ml to 15 ng/ml. Neurotrophic activity was quantified by counting viable differentiated neurons that developed neurites larger than twice the diameter of the perikaryon following 48 h of incubation with different NGF formulations. Data were plotted as mean number of double determinations of differentiated neurons vs. concentration of NGF test formulation and halfmaximal stimulatory activities of NGF (EC50) in several different formulations were determined (Table 1).

TABLE 1

| Halfmaximal stimulatory activity of NGF formulations (EC50) | |
| --- | --- |
| Formulation | EC50 (pg/ml) |
| NGF (no additive) | 75 |
| NGF (0.006% sodium deoxycholate) | 17 |
| NGF (0.02% sodium deoxycholate) | 10 |

These data clearly show that the specific activity of NGF is increased in formulations containing an amphiphilic additive (here: sodium deoxycholate).

Example 4

Pharmaceutical Compositions with Deoxycholate

For the production of the pharmaceutical composition 100 ml of an aqueous solution of 5 mg/ml or 1 mg/ml Hshh (human sonic hedgehog protein) in 50 mmol/l Tris buffer, pH 7.4, are dialysed against formulation solution without deoxycholate for 24 h at 4° C. After dialysis, sodium deoxycholate is added from a stock solution while stirring to obtain an aqueous pharmaceutical composition of 1 mg/ml or 5 mg/ml Hshh in formulation solution. The solution is sterile filtered and stored at 4° C. 0.05 to 2 ml of the solution is used for the injection into man or animals.

4.1 Formulation of Ionically Hydrophobized Hedgehog Protein in Aqueous Phosphate Buffered Saline (Low Sodium Deoxycholate)

Formulation Solution:

| | |
| --- | --- |
| NaCl: | 150 mmol/l |
| Sodium phosphate buffer: | 10 mmol/l |
| Sodium deoxycholate: | 0.05% (w/v) |
| pH: | 7.4 |

4.2 Formulation of Ionically Hydrophobized Hedgehog Protein in Aqueous Phosphate Buffered Saline (High Sodium Deoxycholate)

Formulation Solution:

| | |
|---|---|
| NaCl: | 150 mmol/l |
| Sodium phosphate buffer: | 10 mmol/l |
| Sodium deoxycholate: | 0.1% (w/v) |
| pH: | 7.4 |

4.3 Formulation of Ionically Hydrophobized Hedgehog Protein in Low Ionic Strength Phosphate Buffer (Low Sodium Deoxycholate)

Formulation Solution:

| | |
|---|---|
| NaCl: | 30 mmol/l |
| Potassium phosphate buffer: | 20 mmol/l |
| Sodium deoxycholate: | 0.05% (w/v) |
| pH: | 6.5 |

4.4 Formulation of Ionically Hydrophobized Hedgehog Protein in Low Ionic Strength Phosphate Buffer (High Sodium Deoxycholate)

Formulation Solution:

| | |
|---|---|
| NaCl: | 30 mmol/l |
| Potassium phosphate buffer: | 20 mmol/l |
| Sodium deoxycholate: | 0.1% (w/v) |
| pH: | 6.5 |

Example 5

Pharmaceutical Compositions of Ionically Hydrophobized Hedgehog Protein in Phosphate Buffered Saline With Lipids, Fatty Acids or Steroids For the production of the pharmaceutical composition 100 ml of an aqueous solution of 1 mg/ml or 2 mg/ml Hshh in 50 mmol/l Tris buffer, pH 7.4, are dialysed against formulation solution without lipid, fatty acid or cholate for 24 h at 4° C. After dialysis, 0.01 g of phosphatidate, 0.01 g of phosphatidyl serine, 0.01 g of palmitate, 0.05 g of cholate, 0.05 g of taurodeoxycholate or 0.05 g of taurocholate is added from stock solutions while stirring to obtain an aqueous pharmaceutical composition of 1 mg/ml or 2 mg/ml Hshh in formulation solution. The solution is sterile filtered and stored at 4° C. 0.05 to 2 ml of the solution is used for the injection into man or animals.

Formulation Solution:

| | |
|---|---|
| NaCl: | 150 mmol/l |
| Sodium phosphate buffer: | 10 mmol/l |
| Phosphatidate: | 0.01% (w/v) |
| pH: | 7.4 |

Formulation Solution:

| | |
|---|---|
| NaCl: | 100 mmol/l |
| Sodium phosphate buffer: | 10 mmol/l |
| Phosphatidylserine: | 0.01% (w/v) |
| pH: | 7.4 |

Formulation Solution:

| | |
|---|---|
| NaCl: | 150 mmol/l |
| Potassium phosphate buffer: | 20 mmol/l |
| Sodium palmitate: | 0.01% (w/v) |
| pH: | 7.4 |

Formulation Solution:

| | |
|---|---|
| NaCl: | 150 mmol/l |
| Sodium phosphate buffer: | 10 mmol/l |
| Sodium cholate | 0.05% (w/v) |
| pH: | 7.4 |

Formulation Solution:

| | |
|---|---|
| NaCl: | 100 mmol/l |
| Sodium phosphate buffer: | 10 mmol/l |
| Sodium taurodeoxycholate | 0.05% (w/v) |
| pH: | 7.4 |

Formulation Solution:

| | |
|---|---|
| NaCl: | 150 mM |
| Potassium phosphate buffer: | 20 mM |
| Sodium taurocholate | 0.05% (w/v) |
| pH: | 7.4 |

Example 6

Pharmaceutical Compositions of Ionically Hydrophobized Bone Morphogenetic Protein (BMP-2) in Arginine Buffers For the production of the pharmaceutical composition 100 ml of an aqueous solution of 0.4 mg/ml BMP-2 are dialysed against 500 mmol/l arginine in 10 mmol/l potassium phosphate buffer, pH 6.0, for 24 h at 4° C. After dialysis, 0.01 g (palmitate) or 0.05 g (deoxycholate or taurodeoxycholate) is added from a stock solution while stirring to obtain an aqueous pharmaceutical composition of 0.4 mg/ml BMP in formulation solution. The solution is sterile filtered and stored at 4° C. 0.05 to 2 ml of the solution is used for the injection into man or animals.

Formulation Solution:

| | |
|---|---|
| Arginine | 500 mmol/l |
| Potassium phosphate buffer: | 10 mmol/l |
| Sodium deoxycholate: | 0.05% (w/v) |
| pH: | 6.0 |

Formulation Solution:

| | |
|---|---|
| Arginine | 500 mmol/l |
| Potassium phosphate buffer: | 10 mmol/l |
| Sodium palmitate: | 0.01% (w/v) |
| pH: | 6.0 |

Formulation Solution:

| | |
|---|---|
| Arginine | 500 mmol/l |
| Potassium phosphate buffer: | 10 mmol/l |
| Sodium taurodeoxycholate: | 0.05% (w/v) |
| pH: | 6.0 |

Example 7

Pharmaceutical Compositions of Ionically Hydrophobized Interleukin-2 in Phosphate Buffered Saline For the production of the pharmaceutical composition 100 ml of an aqueous solution of 1 or 2 million IU Interleukin-2 in 50 mmol/l Tris buffer, pH 7.4, are dialysed against formulation solution without the amphiphilic compound for 24 h at 4° C. After dialysis, 0.05 g deoxycholate, 0.01 g phosphatidyl serine or 0.01 g of sodium palmitate is added from stock solutions while stirring to obtain an aqueous pharmaceutical composition of 1 or 2 million IU Interleukin-2 in formulation solution. The solution is sterile filtered and stored at 4° C. 0.05 to 2 ml of the solution is used for the injection into man or animals.

Formulation Solution:

| | |
|---|---|
| NaCl: | 150 mmol/l |
| Sodium phosphate buffer: | 10 mmol/l |
| Deoxycholate: | 0.05% (w/v) |
| pH: | 7.4 |

Formulation Solution:

| | |
|---|---|
| NaCl: | 150 mmol/l |
| Sodium phosphate buffer: | 10 mmol/l |
| Phosphatidylserine | 0.01% (w/v) |
| pH: | 7.4 |

Formulation Solution:

| | |
|---|---|
| NaCl: | 150 mmol/l |
| Potassium phosphate buffer: | 20 mmol/l |
| Sodium palmitate: | 0.01% (w/v) |
| pH: | 7.4 |

Example 8

Pharmaceutical Compositions of Ionically Hydrophobized Interferon-Alpha in Phosphate Buffered Saline For the production of the pharmaceutical composition 100 ml of an aqueous solution of 4 or 40 million IU of Interferon-α2b in 50 mmol/l Tris buffer, pH 7.4, are dialysed against formulation solution without the amphiphilic substance for 24 h at 4° C. After dialysis, 0.05 g deoxycholate, 0.01 g phosphatidyl serine or 0.05 g taurodeoxycholate is added from a stock solution to obtain an aqueous pharmaceutical composition of 4 or 40 million IU Interferon-α2b in formulation solution. The solution is sterile filtered and stored at 4° C. 0.05 to 2 ml of the solution is used for the injection into man or animals.

Formulation Solution:

| | |
|---|---|
| NaCl: | 150 mmol/l |
| Sodium phosphate buffer: | 10 mmol/l |
| Deoxycholate: | 0.05% (w/v) |
| pH: | 7.4 |

Formulation Solution:

| | |
|---|---|
| NaCl: | 100 mmol/l |
| Sodium phosphate buffer: | 10 mmol/l |
| Phosphatidylserine: | 0.01% (w/v) |
| pH: | 7.4 |

Formulation Solution:

| | |
|---|---|
| NaCl: | 150 mmol/l |
| Potassium phosphate buffer: | 20 mmol/l |
| Sodium taurodeoxycholate: | 0.05% (w/v) |
| pH: | 7.4 |

Example 9

Pharmaceutical Compositions of Ionically Hydrophobized Human NGF in Acetate Buffers For the production of the pharmaceutical composition to 100 ml of an aqueous solution of 1 or 2 mg/ml human NGF in 100 mmol/l sodium acetate buffer, pH 6.0, are added 0.05 g deoxycholate, 0.01 g phosphatidate or 0.05 g taurodeoxycholate from a stock solution while stirring to obtain aqueous pharmaceutical compositions. The solution is sterile filtered and stored at 4° C. 0.05 to 2 ml of the solution is used for the injection into man or animals.

Compositions:

| | |
|---|---|
| Human NGF: | 1 mg/ml |
| Sodium acetate buffer: | 100 mmol/l |
| Deoxycholate: | 0.05% (w/v) |
| pH: | 6.0 |
| Human NGF: | 2 mg/ml |
| Sodium acetate buffer: | 100 mmol/l |
| Phosphatidate: | 0.01% (w/v) |
| pH: | 6.0 |
| Human NGF: | 1 mg/ml |
| Sodium acetate buffer: | 100 mmol/l |
| Sodium taurodeoxycholate: | 0.05% (w/v) |
| pH: | 6.0 |

Example 10

Production of an Alginate Gel Containing Hedgehog Proteins

An aliquot of formulation solution of Example 4.1 is stirred with 1% (w/v) aqueous sodium alginate stock solution (Pronova Biopolymer, Norway) in such a way that a gelatinous alginate protein mixture is formed. This gel is directly used as an injectable matrix in an amount of 0.05 to 2 ml.

Example 11

Production of a Collagen Mixture Containing BMP-2

100 µl of one of the formulations solutions of Example 6 is added dropwise onto collagen sponges (Helistat, Integra Life Science, USA) with a size of 10×10×3 mm. The loaded carriers are then frozen (−70° C.) and lyophilized. The sponge is used locally for the healing of bone fractures.

The invention claimed is:

1. An ionic complex precipitate consisting of a hedgehog protein, a sodium deoxycholate, and a buffer.

2. The ionic complex precipitate of claim 1 wherein the hedgehog protein is sonic hedgehog protein and wherein the buffer is selected from the group consisting of sodium phosphate and potassium phosphate.

3. The ionic complex precipitate of claim 1 wherein the hedgehog protein is indian hedgehog protein.

4. The ionic complex precipitate of claim 1 wherein the hedgehog protein is desert hedgehog protein.

5. The ionic complex precipitate of claim 1 wherein the ionic complex precipitate is embedded in a carrier.

6. The ionic complex precipitate of claim 1 wherein the ionic complex precipitate is embedded in a biocompatible carrier.

7. A solid pharmaceutical composition consisting of a hedgehog protein, sodium deoxycholate and a buffer, wherein said composition is obtained from a solution consisting of a hedgehog protein and sodium deoxycholate in the concentration of from 0.01 to 0.1% by weight (w/v), and a buffer.

8. The solid pharmaceutical composition according to claim 7, wherein the hedgehog protein has a concentration of from 1 mg/ml to 5 mg/ml.

9. The solid pharmaceutical composition according to claim 8 wherein the buffer is sodium or potassium phosphate.

* * * * *